United States Patent [19]
Hird et al.

[11] Patent Number: 5,759,569
[45] Date of Patent: Jun. 2, 1998

[54] BIODEGRADABLE ARTICLES MADE FROM CERTAIN TRANS-POLYMERS AND BLENDS THEREOF WITH OTHER BIODEGRADABLE COMPONENTS

[75] Inventors: Bryn Hird; John Collins Dyer, both of Cincinnati; David Harry Melik, Fairfield, all of Ohio

[73] Assignee: The Procter & Gamble Company, Cincinnati, Ohio

[21] Appl. No.: 370,696

[22] Filed: Jan. 10, 1995

[51] Int. Cl.$^6$ .................... A61K 9/70; B32B 5/12; A61L 9/04
[52] U.S. Cl. .......... 424/443; 428/224; 428/113; 604/15; 604/904; 206/323; 206/328; 239/53; 239/54; 239/55; 239/56; 220/DIG. 30
[58] Field of Search ............ 424/443; 523/124, 523/125, 128; 524/35–41, 47, 571; 526/340, 340.1, 340.2, 335, 337, 338, 272, 304.3; 604/373; 272/318.25

[56] References Cited

U.S. PATENT DOCUMENTS

| | | | |
|---|---|---|---|
| Re. 29,873 | 1/1979 | Cunningham | 206/150 |
| 3,454,510 | 7/1969 | Greear et al. | 260/23 |
| 3,592,792 | 7/1971 | Newland et al. | 260/41 |
| 3,778,390 | 12/1973 | Ulrich, Jr. | 260/2.5 AN |
| 3,860,538 | 1/1975 | Guill et al. | 260/2.5 HA |
| 3,867,324 | 2/1975 | Clendinning et al. | 260/23 H |
| 3,883,459 | 5/1975 | Kent | 260/28.5 B |
| 3,887,536 | 6/1975 | Ichikawa et al. | 260/94.2 |
| 3,901,838 | 8/1975 | Clendinning et al. | 260/23 H |
| 3,921,333 | 11/1975 | Clendinning et al. | 47/37 |
| 3,938,656 | 2/1976 | Owen | 206/150 |
| 3,951,884 | 4/1976 | Miyoshi et al. | 260/2.5 B |
| 3,956,424 | 5/1976 | Murayama et al. | 260/876 R |
| 4,016,117 | 4/1977 | Griffin | 260/17.4 ST |
| 4,021,388 | 5/1977 | Griffin | 260/13 |
| 4,049,592 | 9/1977 | Marans et al. | 260/2.5 AD |
| 4,100,122 | 7/1978 | Kent | 260/28.5 |
| 4,125,495 | 11/1978 | Griffin | 260/17.4 ST |
| 4,132,839 | 1/1979 | Marans et al. | 521/159 |
| 4,133,784 | 1/1979 | Otey et al. | 260/17.4 ST |
| 4,144,153 | 3/1979 | Shikinami et al. | 204/159.2 |
| 4,212,955 | 7/1980 | Tobias et al. | 525/5 |
| 4,256,851 | 3/1981 | Taylor et al. | 525/1 |
| 4,324,709 | 4/1982 | Griffin | 523/210 |
| 4,337,181 | 6/1982 | Otey et al. | 523/128 |
| 4,450,198 | 5/1984 | Michaels | 428/315.5 |
| 4,454,268 | 6/1984 | Otey et al. | 524/47 |
| 4,719,246 | 1/1988 | Murdoch et al. | 521/134 |
| 4,766,182 | 8/1988 | Murdoch et al. | 525/413 |
| 4,835,231 | 5/1989 | Yamamori et al. | 526/240 |
| 4,931,488 | 6/1990 | Chiquet | 523/126 |
| 4,983,651 | 1/1991 | Griffin | 524/47 |
| 4,990,541 | 2/1991 | Nielsen et al. | 521/70 |
| 5,037,410 | 8/1991 | Zimmerman et al. | 604/358 |
| 5,059,642 | 10/1991 | Jane et al. | 524/52 |
| 5,065,752 | 11/1991 | Sessions et al. | 128/156 |
| 5,070,122 | 12/1991 | Vanderbilt et al. | 524/47 |
| 5,082,882 | 1/1992 | Pettijohn | 524/47 |
| 5,096,939 | 3/1992 | Mor | 523/125 |
| 5,096,940 | 3/1992 | Mor | 523/125 |
| 5,096,941 | 3/1992 | Harden | 523/126 |
| 5,110,838 | 5/1992 | Tokiwa et al. | 521/81 |
| 5,115,000 | 5/1992 | Jane et al. | 524/47 |
| 5,116,880 | 5/1992 | Tokiwa et al. | 521/134 |
| 5,134,171 | 7/1992 | Hammel et al. | 521/98 |
| 5,162,392 | 11/1992 | Wool et al. | 523/128 |
| 5,171,308 | 12/1992 | Gallagher et al. | 604/372 |
| 5,171,309 | 12/1992 | Gallagher et al. | 604/365 |
| 5,180,765 | 1/1993 | Sinclair | 524/306 |

(List continued on next page.)

FOREIGN PATENT DOCUMENTS

| | | |
|---|---|---|
| 0 430 641 A2 | 6/1991 | European Pat. Off. |
| 0 569 154 A1 | 11/1993 | European Pat. Off. |
| 0 134 464 | 3/1985 | Germany . |
| 5043747 | 2/1993 | Japan ............... C08L 23/00 |
| 7010148 | 1/1995 | Japan ............... B65D 1/09 |

OTHER PUBLICATIONS

Directions for Environmentally Biodegradable Polymer Research, Swift, pp. 105–110, 1993.
Microbiological Deterioration of Rubbers and Plastics, Heap and Morrell, pp. 189–194, 1968.
Rubber–Degrading Enzyme from a Bacterial Culture, Tsuchii and Takeda, pp. 269–274, 1990.
The Effect of Compounding Ingredients on Microbial Degradation of Vulcanized Natural Rubber, Tsuchii, pp. 1181–1187, 1990.
Microbial Degradation of cis–1,4–Polyisoprene, Tsuchii, Suzuki and Takahara, pp. 2441–2446, 1979.
Microbial Degradation of Liquid Polybutadiene, Tsuchii, Suzuki and Takahara, pp. 1217–1222, 1978.
Enhanced Enviromental Degradation of Plastics, Cassidy and Aminabhavi, pp. 89–133, 1981.
The Classification, Preparation, and Utility of Degradable Polymers, Hocking, pp. 35–54, 1992.
Butadiene Deritives, Polymeric, pp 516–519. CA112(17):154104e.
Butadiene Deritives, Polymeric, pp. 516–519. CA107(16):134795z.
CA107(6):41461x.
CA92(11):90582t.
CA90(12):88028g.
CA75(26):152397w.
CA92(11):90582t.
Mechanical Properties of LDPE/Granular Starch Composites*, Willette, pp. 1685–1695, 1994.
Starch/polyolefin blends as environmentally degradable plastics, Pettijohn, pp. 627–629, 1992.

*Primary Examiner*—Joseph L. Schofer
*Assistant Examiner*—Kathryne E. Shelborne
*Attorney, Agent, or Firm*—Carl J. Roof; E. Kelly Linman; Jacobus C. Rasser

[57] ABSTRACT

Biodegradable articles such as diaper topsheets, diaper backsheets, garbage bags, tampon applicators, disposable syringes and the like that are made from trans-1,4-polyisoprene and like trans-polymers. These articles can also be made from blends of these trans-polymers with other biodegradable components such as starch.

54 Claims, No Drawings

U.S. PATENT DOCUMENTS

| | | | |
|---|---|---|---|
| 5,185,009 | 2/1993 | Sitnam | 604/364 |
| 5,190,937 | 3/1993 | Markwell et al. | 514/183 |
| 5,191,734 | 3/1993 | Weber et al. | 47/9 |
| 5,194,581 | 3/1993 | Leong | 528/398 |
| 5,196,247 | 3/1993 | Wu et al. | 428/43 |
| 5,200,247 | 4/1993 | Wu et al. | 428/131 |
| 5,206,087 | 4/1993 | Tokiwa et al. | 428/403 |
| 5,210,108 | 5/1993 | Spinu et al. | 521/182 |
| 5,216,043 | 6/1993 | Sipinen et al. | 523/126 |
| 5,216,050 | 6/1993 | Sinclair | 524/108 |
| 5,217,803 | 6/1993 | McBride et al. | 428/323 |
| 5,219,646 | 6/1993 | Gallagher et al. | 428/287 |
| 5,219,980 | 6/1993 | Swidler | 528/272 |
| 5,227,415 | 7/1993 | Masuda et al. | 524/17 |
| 5,254,607 | 10/1993 | McBride et al. | 524/52 |
| 5,256,711 | 10/1993 | Tokiwa et al. | 524/47 |
| 5,258,422 | 11/1993 | Chang et al. | 523/124 |
| 5,262,458 | 11/1993 | Bastioli et al. | 524/52 |
| 5,286,770 | 2/1994 | Bastioli et al. | 524/52 |
| 5,295,985 | 3/1994 | Romesser et al. | 604/358 |
| 5,308,906 | 5/1994 | Taylor et al. | 524/398 |
| 5,314,754 | 5/1994 | Knight | 428/532 |
| 5,322,866 | 6/1994 | Mayer et al. | 524/47 |
| 5,336,457 | 8/1994 | Wu et al. | 264/171 |
| 5,468,822 | 11/1995 | Tsujimoto et al. | 526/340.1 |

BIODEGRADABLE ARTICLES MADE FROM CERTAIN TRANS-POLYMERS AND BLENDS THEREOF WITH OTHER BIODEGRADABLE COMPONENTS

TECHNICAL FIELD

This application relates to biodegradable articles such as diaper topsheets, diaper backsheets, garbage bags, tampon applicators, disposable syringes and the like that are made from trans-1,4-polyisoprene and like trans-polymers. This application further relates to biodegradable polymer-containing compositions comprising a blend of these trans-polymers with other biodegradable components such as starch.

BACKGROUND OF THE INVENTION

Polymers are used in a wide range of applications due to their stability, elasticity, light weight, strength, ease of fabrication and formulation, and low cost. These applications include packaging, housewares, buildings, highway construction, insulation (sound, vibration, or heat), ground coverings for agricultural weed and erosion control, adhesives, coatings for controlled release products, absorbents, and the like.

Articles made from synthetic polymers are a potential source of nonbiodegradable material that often ends up in landfills or is disposed of improperly in the environment. These articles include flexible packaging materials such as package wraps, garbage bags and the like, foamed products such as Styrofoam insulation, and molded products such as tampon applicators and syringes. These articles are typically derived from thermoplastic polymers such as polystyrene, polyvinyl chloride (PVC), polyethylene and polypropylene. Because these polymers are nonbiodegradable, the products from which they are made will persist in any natural environment into which they are disposed. As a result, products made from synthetic polymers can pose a significant burden on the solid waste stream. Also, articles made from synthetic polymers often are disposed of improperly and persist in the environment as unsightly litter. In addition, these articles (e.g., "six-pack" rings) can be ingested by or become entangled with wildlife as another undesirable effect on the ecosystem.

Environmental concerns have suggested a need for materials having polymer-like properties but without the degree of permanence typically associated with synthetic polymers. The decreasing availability of landfill space, as well as the increased costs of municipal solid waste disposal, have put increasing emphasis on minimizing the impact of nondegradable materials, including synthetic polymers, on the solid waste stream. Man-made polymers are typically not readily degraded by microorganisms that degrade most other forms of organic matter and return them to the biological life cycle. Although synthetic polymers form a relatively small fraction of the materials in landfills today (about 7% by weight or 15–20% by volume, see Thayer, *Chem. Eng. News*, 1989, 67 (4), 7), it would nonetheless be desirable to design such materials so they would be sufficiently durable for their intended use but more susceptible to environmental degradation. This would facilitate the development of methods such as industrial composting to convert municipal solid waste materials to useful products.

There are a number of polymer-based products for which biodegradability and/or compostability would be desirable. For example, films used in packaging, as topsheets and backsheets in diapers, and agricultural ground coverings are intended to survive intact for only a short period of use. Molded articles such as tampon applicators, sanitary napkins, disposable syringes, milk bottles, shopping bags, food wrappers, "six-pack" rings, and the like are often flushed or dumped into sewage systems, septic tanks, or are disposed of improperly in the environment. These articles can remain intact long after disposal due to their resistance to environmental degradation. Ideally, such molded articles would be substantially biodegraded in the sewage system or septic tank, or would decompose at the site of disposal so as to avoid causing visual litter problems or hazards to wildlife.

Plastic film products for agricultural mulching are representative of the problems that can be caused by the persistence of synthetic polymers. Mulching has become an important technique for increasing the yield and quality of vegetable and fruit crops and for decreasing the production costs of these crops. It provides multiple benefits including weed and pest control, as well as control of soil moisture, erosion, nutrient leaching, and soil temperature (frost protection). Polyethylene is the most common polymer used in making agricultural mulch products. Like flexible film products for packaging and garbage bags, these agricultural mulch products can persist for many years. Because the removal, burying or burning of such mulch films is costly, as well as being environmentally "unfriendly," the need for a plastic mulch that can decompose by the end of a growing season is apparent. Improved degradability would also be desirable for "controlled release" of an active from other agricultural products, such as encapsulated pesticides, herbicides, and fertilizers.

Fibers made from synthetic polymers and products fabricated from these fibers are subject to the many of the same waste disposal problems noted previously. Fibers are typically fabricated into woven or nonwoven structures for subsequent use in disposable diapers, sanitary napkins, etc. While fibers derived from wood pulp, cotton, rayon, polyvinyl alcohol, silk, and the like are generally considered to be biodegradable, many nonwovens rely on fibers made from polyethylene and polypropylene that are not biodegradable.

A recently popular form of fiber made from synthetic polymers are those referred to as "bicomponent" fibers. Bicomponent fibers comprise a core fiber made from one polymer that is encased within a thermoplastic sheath made from a different polymer. The polymer comprising the sheath often melts at a different, typically lower, temperature than the polymer comprising the core. As a result, these bicomponent fibers can provide thermal bonding by controlled melting of the sheath polymer, while retaining the desirable strength characteristics of the core polymer. This outer sheath is typically comprised of polyethylene, polypropylene, certain polyesters, and the like, that often have softening and/or melting points in the range of from about 50° to about 200° C. Since products made from thermally bondable fibers are becoming widespread, it would be desirable for such fibers to be biodegradable.

Several approaches to enhance the environmental degradability of polymers have been suggested and tried. These include introduction of photodegradation-sensitizing groups into the molecular structure of the polymer; as well as incorporation of small amounts of selective additives that accelerate oxidative and/or photo-oxidative degradation. Both of these methods have certain problems. Photodegradation functions only if the plastic is exposed to light (e.g., in the case of litter), and provides no benefit if the product is disposed of in a dark environment, e.g., in water, soil or a standard landfill. Oxidative accelerators can cause unwanted changes in the mechanical properties of the polymer, such as embrittlement, prior to or during use.

Another approach that has been suggested, especially for flexible film products such as packaging materials, garbage bags, and agricultural mulch, is the incorporation of particulate biodegradable materials such as starch. See, for example, U.S. Pat. No. 4,016,117 (Griffin), issued Apr. 5, 1977, and U.S. Pat. No. 4,337,181 (Otey et al), issued Jun. 29, 1982. See also Pettijohn, "Starch/Polyolefin Blends as Environmentally Degradable Plastics," Chemtech, 1992, 627; Willett, J. Appl. Polym. Sci., 1994, 54, 1685–1695. In these starch-containing products, the starch particles exposed at or adjacent to the surface of the product are initially biodegraded and leached away. This is followed by successive biodegradation of starch particles at the interior of the product to provide a cellular structure that is more readily attacked by the processes of oxidation, hydrolysis, direct enzyme action or combinations of these processes. The appeal of this approach is that the nonbiodegradable polymer residue is less noticeable. It also provides a higher surface area for this polymer residue that tends to accelerate oxidative and/or photolytic degradative processes. Nonetheless, these starch-containing products still leave behind a nonbiodegradable polymer residue. Indeed, this problem of nonbiodegraded residual polymer components is recognized by the art. See U.S. Pat. No. 5,219,646 (Gallagher et al), issued Jun. 15, 1993.

Another approach to environmental degradability of articles made with synthetic polymers is to make the polymer itself biodegradable or compostable. See Swift, Acc. Chem. Res., 1993, 26, 105–110 for a general overview on biodegradable polymeric compositions. Most of this work has been based on hydrolyzable polyester compositions, chemically modified natural polymers such as cellulose or starch or chitin, and certain polyamides. See, for example, U.S. Pat. 5,219,646 (Gallagher et al), issued Jun. 15, 1995 (blend of hydrolyzable polyester and starch). Polyvinyl alcohol is the only synthetic high molecular weight addition polymer with no heteroatom in the main chain generally acknowledged as biodegradable. See also Hocking, J. Mat. Sci. Rev. Macromol. Chem. Phys., 1992, C32(1), 35–54, Cassidy et al, J. Macromol. Sci.—Rev. Macromol. Chem., 1981, C21(1), 89–133, and "Encyclopedia of Polymer Science and Engineering," 2nd. ed.; Wiley & Sons: New York, 1989; Vol. 2, p 220. (Limited reports add poly (alkyl 2-cyanoacrylates) to this list of biodegradable synthetic polymers.)

Natural rubber (cis-1,4-polyisoprene) is also readily biodegradable. Natural rubber retains carbon-carbon double bonds in the main polymeric chain that are believed to facilitate attack by either oxygen and/or microbes/fungi, leading subsequently to chain scission, molecular weight reduction, and eventually total degradation of the polymer. See Heap et al, J. Appl. Chem., 1968, 18, 189–194. The precise mechanism for the biodegradation of natural rubber is not known. Enzymatic and/or aerobic oxidation of the allylic methyl substituent may be involved. See Tsuchii et al., Appl. Env. Micro. 1990, 269–274, Tsuchii et al., Agric. Biol. Chem., 1979, 43(12), 2441–2446, and Heap et al, supra. By contrast, nonbiodegradable polymers such as polyethylene, polypropylene, polyvinyl chloride, polyacrylonitrile, poly(meth)acrylates and polystyrene have saturated carbon-carbon backbones that do not facilitate attack by either oxygen and/or microbes. This biodegradability has been recognized only for the natural form of rubber. See Tsuchii et al., supra, which reports: "Synthetic polyisoprenes, however, were not degraded completely by the organism." More recently, it was reported that synthetic "cis-1,4-polyisoprene does not undergo specific biodegradation." See Kodzhaeva et al., Intern. J. Polymeric Mater., 1994, 25, 107–115.

Unfortunately, natural rubber is biodegradable to the extent that it is too unstable for most uses. Natural rubber also suffers from poor mechanical properties (e.g., strength, creep resistance). Indeed, stabilizers, fillers, and/or crosslinking agents are routinely added to natural rubber to enhance its mechanical properties. Crosslinkers are typically required in order to provide sufficient mechanical integrity for practical use. However, the most common crosslinking process creates a polysulfide linkage, i.e., by vulcanization, that virtually eliminates the biodegradability of natural rubber. See Tsuchii et al. J. Appl. Polym. Sci., 1990, 41, 1181–1187. Crosslinked natural rubber is also elastomeric and thermosetting, thus making it unsuitable for blown or extruded films, injection molded articles, fibers or other melt-processed articles.

Accordingly, it would be desirable to provide polymer-containing products that: (1) are biodegradable in the environment, as well as biodegradable or compostable during municipal composting operations; (2) are thermoplastic so that they can be molded, cast, extruded, or otherwise melt-processed into various forms including films, fibers, coatings, foams, and the like; (3) can be manufactured at reasonable cost; (4) have sufficient toughness, strength and stability during use until appropriately disposed of.

DISCLOSURE OF THE INVENTION

The present invention relates to biodegradable compostable articles that at least partially comprise certain biodegradable thermoplastic trans-polymers. These trans-polymers have a weight average molecular weight ($M_w$) of at least about 20,000 and are made by polymerizing a monomer component that comprises:

(1) from about 70 to 100 mole % 1,3-dienes selected from 1,3-butadiene, 2-methyl-1,3-butadiene (isoprene), 2,3-dimethyl-1,3-butadiene, 2-methyl-3-ethyl-1,3-butadiene, 2-methyl-3-propyl-1,3-butadiene, 2-phenyl-1,3-butadiene, 2,3-diphenyl-1,3-butadiene, 1,3-pentadiene (piperylene), 2-methyl-1,3-pentadiene, 2,3-dimethyl-1,3-pentadiene, 2-methyl-3-ethyl-1,3-pentadiene, 2-methyl-3-propyl-1,3-pentadiene, 1,3-hexadiene, 7-methyl-3-methylene-1,6-octadiene (beta-myrcene), 2,6-dimethyl-1,5,7-octatriene (ocimene), and mixtures thereof; and (2) up to about 30 mole % other compatible comonomers.

The present invention further relates to certain polymer-containing compositions useful in making these biodegradable and/or compostable articles. These compositions comprise a combination of:

(1) from about 20 to about 99% by weight of these thermoplastic trans-polymers; and (2) from about 1 to about 80% by weight of another biodegradable component.

Without being bound by theory, it is believed the biodegradability, or at least compostability, of the trans-polymers of the present invention is due to the similarity of the main chain of the polymer to that of trans-1,4-polyisoprene present in natural materials such as gutta percha and balata. Like gutta percha and balata, (as well as natural rubber); the polymers of the present invention retain a double bond in the main polymeric chain. This double bond is believed to be essential for attack by either oxygen and/or microorganisms such that the polymer chain is broken up into smaller units for subsequent degradation.

The trans-configuration in the polymers of the present invention is important because it allows the polymer chains to pack together into crystalline domains resulting in a material that is semicrystalline, i.e., partially crystalline and partially amorphous. The semicrystalline nature of these materials imparts the desired degree of strength, toughness, and integrity without crosslinking the polymer. (Crosslinking of the polymer would convert it to a thermoset that could no longer be cast, extruded, molded or otherwise melt-processed. Crosslinking can also to inhibit or prevent biodegradation.) The absence of crosslinks facilitates ease of processing, relatively low cost, and complete biodegradability of articles comprising these trans-polymers.

The biodegradable articles of the present invention can be manufactured in a variety forms including thin films (e.g., sheets), fibers, foams, latexes, and shaped articles formed by injection molding, blow molding, vacuum forming, extrusion, pulltrusion, etc. Examples of articles utilizing films or sheets include flexible packaging materials, shopping bags, dust bags, garment bags, garbage and lawn waste bags; carriers comprising a plurality of connected annular sections where each annular section is capable of releasably securing a container (e.g., "six-pack" rings), ground coverings, agricultural mulch and other agricultural film products containing seeds, pesticides, herbicides, and the like; components of disposable absorbent articles (e.g., diapers, sanitary napkins, etc.) such as topsheets, backsheets; and various other disposable products such as adhesive tape substrates, laminates garment articles such as protective clothing, surgical drapes, surgical gowns, surgical sheets, and the like. Examples of articles utilizing fibers include thermally bondable bicomponent fibers, woven, knitted and nonwoven fabrics useful for wipes etc., as well as core components in absorbent articles such as diapers. Examples of articles made from foamed polymers include insulation components, loose-fill packing components (peanuts), foamed plastic products such as food packaging, and surgical sponges. Examples of articles made from latexes include binders and coatings such as those used on glossy paper. Examples of articles formed by injection molding, blow molding, vacuum forming, or other melt-processing techniques include tampon applicators, disposable syringes, toys, containers, bottles, cartons, pipes or tubes, pellets containing various active ingredients intended for slow release resulting from bioerosion; and the like.

DETAILED DESCRIPTION OF THE INVENTION

A. Definitions

As used herein, the term "biodegradation" refers to the natural process of a material being degraded under aerobic/anaerobic conditions in the presence of fungi, bacteria, actinomycetes and other microorganisms to carbon dioxide/methane, water, and biomass. (Biodegradable materials containing heteroatoms can also yield other products such as ammonia or sulfur dioxide.) "Biomass" is generally understood to account for the portion of the metabolized materials that is incorporated into the cellular structure of the organisms present or converted to humus fractions indistinguishable from material of biological origin.

As used herein, the term "biodegradability" refers to the propensity of a material to biodegrade; i.e., the rate and extent of degradation. Generally, a synthetic material can be considered biodegradable if the rate and extent of biodegradation is comparable to that of naturally occurring materials (e.g., leaves, grass clippings, sawdust) or to synthetic polymers that are generally recognized as biodegradable in the same environment.

As used herein, the term "composting" refers to a human controlled aerobic/anaerobic process (e.g., a municipal solid waste (MSW) composting facility) where material undergoes physical, chemical, and/or biological degradation to carbon dioxide/methane, water, and biomass. Composting is generally conducted under conditions ideal for biodegradation to occur, e.g., disintegration to small pieces, temperature control, inoculation with suitable microorganisms, aeration as needed, and moisture control. A composting process typically requires about 6 months for the incoming material to mature to compost and involves about a 50% reduction in mass, the balance being lost to the gases listed above (and water vapor). See Haug, Roger T. "Compost Engineering"; Technomic Publ.: Lancaster, Pa., 1980.

As used herein, the term "compostability" refers to the biodegradability of a material under specific composting conditions (e.g., temperature, moisture level, oxygen level, pH, time, agitation, etc.). Materials can more readily biodegrade under optimized composting conditions relative to aerobic/anaerobic conditions in soil. However, even after 6 months of aerobic composting of materials such as yard waste, only half of the total mass is completely mineralized to carbon dioxide/methane and water. The residue comprises potentially usable "compost" that contains slower degrading matter and partially degraded biomass.

As used herein the term "mineralized" means that the carbon in the material is metabolized to yield carbon dioxide. "Percent mineralization" refers to the percentage of carbon atoms in a sample which are converted to carbon dioxide. Conversion to biomass is not represented by this fraction.

As used herein, the term "1,3-diene" refers to a compound having two carbon-to-carbon double bonds where these double bonds are in the 1,3-position.

As used herein, the term "trans-polymer" refers to a polymer with carbon-to-carbon double bonds in the polymer backbone where these double bonds are predominantly in the trans configuration and the polymer is at least partially crystalline. In a biodegradable trans-polymer, the residual sequences of repeat units that remain upon chain cleavage at the sites of unsaturation in the polymer backbone are also completely biodegradable. These trans-polymers can be linear or branched, can be homopolymers or copolymers, and can have random, alternating, block, segmented, or graft architectures. These trans-polymers can also have various morphologies such as lamellar, spherical, or cylindrical.

As used herein, the term "elastomer" and "elastomeric" refer to polymers that can easily undergo very large reversible deformations under applied load. This property appears when either chemical or physical crosslinks are present in the polymeric system. For example, polyisoprene (natural rubber) can be readily formed into a typical elastomer. It is amorphous, easily crosslinked, and has a low Tg (ca.—73° C. as the cis isomer). See Odian, "Principles of Polymerization" 3rd ed.; Wiley & Sons: N.Y., N.Y., 1991, pp 35–37.

As used herein, the term "plastic" refers to polymers that have a wide range of mechanical behaviors typically between those of elastomers and high modulus fibers. Like elastomers, plastics can exhibit very large strain at failure. However, unlike elastomers, very little of this strain is recoverable. Flexible plastics typically have medium to high degrees of crystallinity with a Tg below room temperature, and a relatively large difference between glass transition and melting temperatures. (See Odian, supra, page 620.) For example, polyethylene, polypropylene, trans-polyisoprene, and many polyesters have the characteristics of a typical flexible plastic.

As used herein, the term "thermoplastic" refers to polymers that flow and deform under high temperature and pressure without recovery of their original shape. Conversely, as also used herein, the term "thermoset" refers to a polymer that cannot flow under thermal or mechanical stress and is usually crosslinked. See Odian, supra, page 109.

As used herein, the term "comprising" means that the various monomers, and other components, or steps, can be conjointly employed in practicing the present invention. Accordingly, the term "comprising" encompasses the more restrictive terms "consisting essentially of" and "consisting of."

All percentages used herein that relate to monomer compositions of polymers are by mole percent unless otherwise specified. All other percentages, ratios and proportions used herein are by weight unless otherwise specified.

B. Determining the Biodegradability of Polymers

A variety of test methods have been used to evaluate the biodegradability of synthetically derived polymers. (See Andrady, *J. Materials Sci.—Rev. Macromol. Chem. Phys.* 1994, C34(1), 25–76.) Some methods rely on exposing the synthetic polymer to environmental conditions and subsequently making physical integrity measurements over time. Loss of physical strength or related property is used as evidence of "biodegradability." This technique more properly determines the "biodisintegratability" of the material. However, it does not determine the ultimate fate of residual small pieces of undegraded polymer. The presence of such undegraded residue is potentially significant, especially when repeated use in the same area results in a gradual accumulation of high levels of the particular polymer.

Another test used widely to assess biodegradability is the Sturm test (See Swisher, R. D. "Surfactant Biodegradation" 2nd ed.; Dekker:New York, 1987, Vol. 18, Chapter 5). In this test, the target compound is added to a dilute medium containing only inorganic nutrients and inoculated microorganisms common to municipal sewage solutions. This is a "sole source" test where the only carbon source for metabolism is the target compound. The amount of carbon dioxide produced over time (mineralization) can be related to the ability of the microorganisms to utilize the carbon in the target compound their metabolic processes, and can be considered to be true evidence of biodegradation if enough evolves over time. However, even readily biodegradable materials are not completely mineralized in this test. Typically, 10–20% of these materials are converted into "biomass" that is not measured in the Sturm test. Also, compounds that are not soluble in water can only be degraded at the exposed surface, inducing a kinetic limitation. Finally, the inoculate and medium of this test do not adequately approximate the diverse microorganisms available in other waste streams, such as municipal solid waste compost. False negatives can be produced from samples that are biodegradable when exposed only to organisms and/or matrices that are not found in the Sturm test with sewerage inocula. For example, a natural solid material such as pine sawdust that is known to be biodegradable is only mineralized 10% in a Sturm test after 90 days. However, if a Sturm test shows significant evolution of carbon dioxide (e.g., at least 5%) from a homogeneous material relative to a control (i.e., without substrate), the material is typically regarded as being inherently biodegradable.

For the purposes of the present inventions, if a homogeneous homopolymer has a level of mineralization (i.e., percent conversion of carbon to carbon dioxide) of at least 5% within a 90 day period in an aerobic test, it is considered to be inherently biodegradable. This 5% level should be in excess of contributions from any known biodegradable adjuvant materials, such as emulsifiers or processing aids, that can be present in the polymer. In other words, the mineralization level of the polymer should not be "artificially" enhanced by the presence of other readily biodegradable materials. Although 5% mineralization within 90 days may not be considered very stringent, many materials widely acknowledged as being biodegradable barely meet this criterion whereas those which show minimal mineralization are generally recognized as being non-biodegradable.

Ideally, the extent of mineralization of the biodegradable polymer will be greater than 5% and the rate biodegradation will be significant, even at the end of the 90 day period. Factors other than the chemical makeup of the polymer should be taken account to ensure representative results. Two of the most significant are: (a) the surface area of the test solid; and (b) the hydrophilicity of its surface. These factors may not alter the ultimate fate of the test material, but can affect the rate of mineralization.

Materials that are not biodegradable nearly always show very low levels of mineralization (i.e., less than 5%, and often less than 1–2%, in 90 days). For example, polystyrene is mineralized less than about 1% after 90 days in the Sturm test. This value is typical of materials not considered to be biodegradable and reflects the "noise" inherent in the results of the test.

Mineralization data for copolymers, polymer blends, and non-homogeneous polymers (e.g. semicrystalline homopolymers such as trans-1,4-polyisoprene) require careful scrutiny in order to determine whether these materials are inherently biodegradable. In the case of copolymers and blends, care must be taken to ensure that all of the components are biodegrading. Typically this requires much higher levels of biodegradation than for systems containing only one component. In the case of semicrystalline homopolymers, the amorphous regions typically biodegrade at a greater rate than the crystalline regions. However, if the polymer is inherently biodegradable, the crystalline regions will ultimately biodegrade, albeit at a slower rate than the amorphous regions. The rate of biodegradation can be enhanced if the melting point of such crystalline regions is approached or exceeded during the biodegradation process (e.g., in composting). Thus a semicrystalline homopolymer such as trans-1,4-polyisoprene that exhibits greater than 5% mineralization within 90 days in a Sturm test is considered to be inherently biodegradable.

C. Biodegradable Trans-Polymers

The biodegradable trans-polymers useful in the present invention are made from a monomer that comprises: (1) certain 1,3-dienes; and (2) optionally other compatible comonomers. Suitable 1,3-dienes include 1,3-butadiene, 2-methyl-1,3-butadiene (isoprene), 2,3-dimethyl-1,3-butadiene, 2-methyl-3-ethyl-1,3-butadiene, 2-methyl-3-propyl-1,3-butadiene, 2-phenyl-1,3-butadiene, 2,3-diphenyl-1,3-butadiene, 1,3-pentadiene (piperylene), 2-methyl-1,3-pentadiene, 2,3-dimethyl-1,3-pentadiene, 2-methyl-3-ethyl-1,3-pentadiene, 2-methyl-3-propyl-1,3-pentadiene, 1,3-hexadiene, diterpenes such as beta-myrcene (7-methyl-3-methylene-1,6-octadiene) and ocimene (2,6-dimethyl-1,5,7-octatriene), and mixtures thereof. Examples of preferred 1-3-dienes include isoprene, 1,3-butadiene and 2,3-dimethyl-1,3-butadiene.

Polymers useful in the present invention can be made using other compatible comonomers (i.e., copolymerizable comonomers) in addition to the 1,3-diene. These optional compatible comonomers typically modify the glass transition properties of the resulting polymer, the melting point (Tm), the rate of crystallization, and its mechanical properties, including tensile, tear and impact properties. These comonomers should also not substantially affect the biodegradability or compostability of the resulting polymer. Suitable optional comonomers include those having a double bond that will copolymerize with the 1,3-diene. Illustrative copolymerizable monomers of this type include alpha-olefins such as ethylene, propylene, 1-butene 4-methyl-1-pentene; cyclic unsaturated compounds such as cyclopentene, dicyclopentadiene, or pinene; styrene and styrene derivatives such as alkyl styrenes; acrylic, alpha-alkyl acrylic, and alpha-cyano acrylic acids, and the esters, amides and nitriles thereof, such as methyl acrylate, ethyl acrylate, butyl acrylate, n-octyl acrylate, 2-ethylhexyl acrylate, methyl methacrylate, butyl methacrylate, octyl methacrylate, nonyl methacrylate, decyl methacrylate, isodecyl methacrylate, dodecyl (lauryl) methacrylate, tetradecyl methacrylate, acrylamide, N-methylacrylamide, N,N-dimethylacrylamide, N,N-dimethyl-methacrylamide, acrylonitrile, methacrylonitrile, and the like; maleic and fumaric acids, their anhydrides, and their alkyl esters such as maleic anhydride, dimethyl maleate; esters of vinyl alcohol such as vinyl acetate and vinyl propionate; and the like, as well as mixtures of these monomers.

The monomer component used in preparing polymers according to the present invention can comprise from about 70 to 100 mole % 1,3-diene and from 0 to about 30 mole % of these compatible comonomers. Typically, this monomer component comprises from about 80 to 100 mole % 1,3-diene and from 0 to about 20 mole % of these compatible comonomers, and more typically from about 90 to 100 mole % 1,3-diene and from 0 to about 10 mole % of these compatible comonomers. Preferably, the polymers useful in the present invention are made exclusively from the 1,3-diene (i.e., monomer component is 100 mole % 1,3-diene).

Polymers useful in the present invention are generally prepared by polymerizing the monomer(s) using a suitable initiator in a solvent suitable for forming mostly trans polymers. For a general description of processes for preparing such trans-polymers, see Odian, supra, p 663–667, and McGrath, *J. Chem. Ed.*, 1981, 58(11), 844. See also L. Porri and A. Giarrusso in "Comprehensive Polymer Science," Vol. 4, G. Allen and J. C. Bevington, Eds.; Pergamon Press, Oxford, 1989, pp 54–99. Suitable initiators include transition metal catalysts and free radical initiators. Solvents that favor the trans configuration are typically nonpolar, such as n-pentane.

Suitable transition metal catalysts include: a) catalysts derived from aluminum alkyls or aluminum hydrides and transition metal compounds (Ziegler-Natta catalysts including metallocene catalysts); b) catalysts derived from precursors not containing metal-carbon bonds, and c) catalysts based on allyl derivatives of transition metals.

Representative Ziegler-Natta catalysts include vanadium halides such as $VCl_3$, $VOCl_3$ and $VCl_4$, in conjunction with aluminum alkyls ($AlR_3$, $AlR_2Cl$); which give heterogeneous catalyst systems that are highly specific for the trans polymerization of 1,3-dienes. These catalyst can be supported on an inert support to increase polymer yields. Soluble vanadium catalysts can be prepared from $V(acac)_3$, or other soluble vanadium compounds, as well as $AlR_2Cl$ or $AlRCl_2$. Other catalysts which give high trans polyisoprene have been obtained from $Ti(OR)_4$, $VCl_3$ and $AlR_3$. Some non-vanadium catalyst systems include $Nd(CH_2Ph)_3$, or those obtained by reacting $Al(Bu^i)_3$ with $Nd(OR)_3$ or $Nd(OCOR)_3$; or by reacting $MgR_2$ with $Nd(OCOR)_3$.

Representative catalysts derived from precursors not containing metal-carbon bonds include rhoduim salts such as $RhCl_3.3H_2O$, and $Rh(NO_3)_3.2H_2O$, which are active in aqueous emulsions or in protic solvents and give trans-1,4 polymers.

Representative catalysts based on allyl derivatives of transition metals include (allyl)NiBr, and (allyl)NiI which yield high trans polymers in the appropriate solvent. Allyl derivatives of other transition metals such as Ti, Zr, Mo, W, Ru, Rh, U, and Nd are also effective catalysts for 1,3-dienes. The addition of electron donors such as ethers, water, alcohols, and phosphites to allyl derivatives of transition metals causes an increase in the trans content of the resultant polymer.

Representative free radical initiators include benzoyl peroxide, azo-bis-isobutyronitrile, and potassium persulfate. The degree of trans polymer produced via this technique tends to decrease with increasing temperature of the reaction.

Besides the monomers and the initiator, various optional adjuvants can be used in preparing polymers according to the present invention. These optional adjuvants typically are included for the purpose of modifying the stability, color, strength, or other properties of the resultant polymer. Suitable adjuvants include antioxidants such as Hindered Amine Light Stabilizers (HALS), for example bis-(1,2,2,5,5-pentamethylpiperidinyl)sebacate (Tinuvin 765), phenolic antioxidants, for example t-butylcatechol, as well as other antioxidants such as triethyl phosphite and t-butylhydroxyquinone. Surprisingly, it has been found that the inclusion of these antioxidants can in some cases promote the biodegradability of the polymers. Without being bound by theory, it is believed these adjuvants prevent the premature autooxidation of the unsaturated polymer chain leading to crosslinking and associated attenuation in the required elements for biodegradation described hereinabove.

Other optional adjuvants that can be included are those that enhance the degradability of the trans-polymer upon exposure to light, particularly ultraviolet light in sunlight. Such adjuvants are well known in the art and typically include vinyl ketone or carbonyl monoxide moieties as part of a polymer chain. See, for example, U.S. Pat. No. 3,860,538 (Guillet et al), issued Jan. 14, 1975 (herein incorporated by reference) which discloses a wide variety of such polymers made with "keto carbonyl" groups, including those made from butadiene, isoprene, pentadiene, and hexadiene. Alternatively, additives such as benzophenone, anthrone, anthraquinone, xanthone, 3-ketosteroids; and hydroxy substituted 2,4-pentadienophenones can be included. See U.S. Pat. No. 3,888,804 (Swanholm et al), issued Jun. 10, 1975, which is incorporated by reference.

Another optional adjuvant that can be included is a compound that promotes the oxidation of the trans-polymer, thus leading to its biodegradability. These are often called "prooxidants" and are typically the transition metal salts of organic acids, e.g., stearates, naphthenates, oleates, and others. See U.S. Pat. No. 4,983,651 (Griffin), issued Jan. 8, 1991; U.S. Pat. No. 3,592,792 (Newland et al), issued Jul. 13, 1971, U.S. Pat. No. 3,454,510 (Greear et al), issued Jul. 8, 1969; U.S. Pat. No. 5,096,941 (Harnden), issued Mar. 17, 1992; U.S. Pat. No. 3,951,884 (Miyoshi, et al) issued Apr. 20, 1976; U.S. Pat. No. 3,956,424 (Iizuka et al) issued May 11, 1976; U.S. Pat. No. 5,096,941 (Harnden) issued Mar. 17, 1992; all of which are incorporated by reference.

Other adjuvants that can be included are plasticizers, slip agents, antistatic agents, release agents, tackifiers, dyes, pigments, flame retardants, fillers such as carbon black, calcium carbonate, silicates, opacifiers such as titanium dioxide, and other additives well known to those skilled in the art. Suitable plasticizers include dioctyl azelate, dioctyl sebacate, or dioctyl adipate and other long chain length alkyl esters of di-, tri-, and tetra-carboxylic acids such as azelaic, sebacic, adipic, phthalic, terephthalic, isophthalic, and the like. Effective amounts of these plasticizers are typically in the range of from about 5 to 30% by weight of the trans-polymer, more typically from about 7 to about 15% by weight of the trans-polymer. Suitable slip agents are those commonly derived from amides of fatty acids having about 12 to 22 carbon atoms. Such agents augment the antiblocking properties of films and are commonly incorporated in amounts of from about 0.05 to about 3% based on the dry weight of the films when used. Suitable antistatic agents include ethoxylated amines and quaternary amine salts having organic constituents of about 12–18 carbon atoms in length. Agents of this type slowly diffuse to the surface of the polymer and, because of their ionic character, form an electrically conductive layer on the surface. Antistatic agents are commonly incorporated in amounts of from about 1 to about 5% based on the dry weight of the films when used.

The trans-polymers useful in the present invention have a fairly high $M_w$. These trans-polymers generally have a $M_w$ of at least about 20,000. Preferred trans-polymers have a $M_w$ of at least about 50,000. Typically, these trans-polymers have a $M_w$ in the range of from about 50,000 to about 1,000,000, more typically from about 200,000 to about 600,000.

D. Biodegradable Polymer Compositions Having Other Biodegradable Components

The biodegradable trans-polymers useful in the present invention can be combined with other biodegradable components by mixing, laminating, blending, coextrusion, etc., to provide biodegradable polymer-containing compositions that can be subsequently formed into biodegradable articles. These biodegradable polymer-containing compositions comprise from about 20 to about 99% by weight trans-polymer as previously described and from about 1 to about 80% by weight of another biodegradable component. Typically, these biodegradable polymer-containing compositions comprise from about 30 to about 95% by weight trans-polymer and from about 5 to about 70% by weight the other biodegradable component, more typically from about 50 to about 90% by weight trans-polymer and from about 10 to about 50% by weight the other biodegradable component. The precise amounts of trans-polymer and other biodegradable component present in the biodegradable polymer-containing composition will depend upon a number of factors, including the particular article to be made from the composition and its intended use.

These other biodegradable components suitable for use in the present invention include water-soluble polymers such as polyvinyl alcohol; hydrolyzable polymers including hydrolyzable aliphatic polyesters such as polyethylene adipate, poly(1,3-propanediol adipate), poly(1,4-butanediol adipate), poly(1,4-butanediol sebacate), poly(1,3-propanediol succinate), and poly(1,4-butanediol glutarate) and hydrolyzable aliphatic polyurethanes such as those derived from epsilon-caprolactone or the reaction products of an aliphatic diol-dicarboxylic acid condensation, e.g., those derived from polyethylene glycol adipate, poly(1,3-propanediol adipate) and poly (1,4-butanediol adipate); other biodegradable polymers such as cis-polyisoprene and cis-polybutadiene, poly(caprolactone), poly(lactic acid), poly(hydroxy alkanoates) such as the homopolymers of 3-hydroxybutyrate and 4-hydroxybutyrate, and the copolymers of hydroxybutyrate with other hydroxy acids, for example, 3-hydroxypropionate, 3-hydroxyvalerate, 3-hydroxyhexanoate, 3-hydroxyoctanoate, or longer chain hydroxy acids (e.g., $C_9$–$C_{12}$ hydroxy acids), starch, natural rubber, gutta percha, balata, dextran, chitin, cellulose, wood flour, derivatives of biodegradable polymers including cellulose esters such as chitosan, cellulose nitrate, cellulose acetate, and block copolymers of polycaprolactone with polydienes; and the like. See U.S. Pat. No. 5,216,043 (Sipinen et al), issued Jun. 1, 1993 and U.S. Pat. No. 3,921,333 (Clendinning et al), issued Nov. 25, 1975 (herein incorporated by reference), which disclose various biodegradable polymers. These other biodegradable components can be a single polymer, compound, or composition, or can be a mixture of different biodegradable components. Particularly preferred biodegradable components include dextran, cis-polyisoprene and starch.

Suitable starches include any unmodified starch from cereal grains or root crops such as corn (e.g., zein), wheat, rice, potato, and tapioca. The amylose and amylopectin components of starch as well as modified starch products such as partially depolymerized starches and derivatized starches can also be used. The term "starch" encompasses all such starches, including starch components, modified starch products, and starch degradation products. The terms "modified starch" and "starch degradation products" include for example pregelatinized starches (cold swelling starch), acid modified starches, oxidized starches, slightly crosslinked starches, starch ethers, starch esters, dialdehyde starches, and degradation products of starch hydrolyzed products and dextrenes.

The particle size of the starch granules can, however, limit some of the attainable physical dimensions of certain articles, such as the gauge of thin films and coatings and the diameter of fibers. To facilitate the preparation of thinner films and fibers, the particle size of starches can be decreased by grinding with oversized particles being removed by procedures such as air classification. In addition, starch granules can be modified by treatments such as pregelatinization in which concentrated starch/water slurries are dried quickly by drum drying, spray drying, foam heat or puff extrusion. The pregelatinized starch can be dried and optionally ground and classified to yield fine starch particles. Other biodegradable derivatives of starch can be treated similarly. If desired, a mixture of two or more starches can be used.

In the preparation of the films, it is preferred that the starch be gelatinized. Gelatinization can be achieved by any known procedure such as heating in the presence of water or an aqueous solution at temperatures above about 60° C., until the starch granules are sufficiently swollen and disrupted that they form a smooth viscous dispersion in the water. The gelatinization can be carried out either before or after admixing the starch with the trans-polymer.

In preparing the polymer-containing compositions, the starch (e.g., starch granules) is normally mixed or otherwise blended with the raw trans-polymer during processing to provide a composition suitable for casting, extruding, molding, or other fabrication procedure. If the polymerization takes place under conditions such that the starch is not altered chemically or physically, the starch granules can also be added to the monomer.

E. Preparation of Biodegradable Articles from Trans-Polymers and Blends Thereof with Other Biodegradable Components Such as Starch The films, fibers, foams and latexes made from these trans-polymers, or blends of these trans-polymers with other biodegradable components such as starch, have a great number of uses in products where biodegradability is desired. In addition, these polymers and blends can be used to make other shaped articles by injection molding, blow molding, thermal forming of sheets, rotational molding of powder, extrusion, pultrusion, etc. The following is a non-exclusive list of such end uses and articles: agricultural mulch; other agricultural film products containing seeds, fertilizers, pesticides, herbicides, and the like; adhesive tape substrates; bed sheets; containers, bottles, and cartons; disposable diapers; film products including flexible packaging materials; shopping bags, dust bags, garment bags, garbage bags, lawn waste bags, and industrial bags; labels and tags; monofilaments; pillow cases; protective clothing; surgical drapes, gowns, sheets and sponges; tampon applicators; disposable syringes; temporary enclosures and temporary siding; toys; wipes; foamed plastic products such as food packaging, foamed packing components, bottles or containers prepared by injection molding or vacuum forming; pellets containing various active ingredients intended for slow release resulting from bioerosion, strips or tabs containing pesticides and repellents that bloom to the surface for controlled release such as flea collars or cattle ear tags, and like articles.

The films, fibers, foams and nonwoven fabrics prepared from the polymers and blends of the present invention have particular utility in disposable absorbent articles. By "absorbent article" herein is meant a consumer product that is capable of absorbing significant quantities of urine or other fluids, like aqueous fecal matter (runny bowel movements), discharged by an incontinent wearer. Examples of such absorbent articles include disposable diapers, incontinence garments and pads, catamenials such as tampons and sanitary napkins, disposable training pants, bed pads, clothing shields, and the like. Absorbent article components that can be made from the polymers and blends of the present invention include backsheets; topsheets, fastening tapes, frontal landing strips, hot melt adhesives used to bond these various components to one another, leakage shields used at the (diaper) waist in the front and back, absorbent core components such as fibers and nonwoven absorbent layers, and packaging materials for these articles.

These absorbent articles typically comprise a fluid impervious backsheet, a fluid pervious topsheet joined to, or otherwise associated with the backsheet, and an absorbent core positioned between the backsheet and the topsheet, where at least one of the topsheet and backsheet and preferably both are films or nonwovens made from the trans-polymers of the present invention, or blends of these trans-polymers with other biodegradable components such as starch. The topsheet is positioned adjacent to the body surface of the absorbent core. The topsheet is preferably joined to the backsheet by attachment means such as those well known in the art. In preferred absorbent articles, the topsheet and the backsheet are joined directly to each other at the periphery thereof. See U.S. Pat. No. 3,860,003 (Buell), issued Jan. 14, 1975; U.S. Pat. No. 4,808,178 (Aziz et al), issued Feb. 28, 1989; U.S. Pat. No. 4,695,278 (Lawson), issued Sep. 22, 1987; and U.S. Pat. No. 4,816,025 (Foreman), issued Mar. 28, 1989, (all of which are incorporated by reference) for some representative diaper configurations.

The backsheet is typically impervious to body fluids and is preferably manufactured as a thin flexible film. The backsheet prevents body fluids absorbed and contained in the absorbent core from wetting articles that contact the absorbent article such as pants, pajamas, undergarments, and the like. The backsheet can be in the form of a woven or nonwoven material, a film, or a composite material such as a film-coated nonwoven material. Preferably, the backsheet is a film having a thickness of from about 0.012 mm (0.5 mil) to about 0.051 mm (2.0 mils). The backsheet is preferably embossed and/or matte finished to provide a more clothlike appearance. Further, the backsheet can be modified to permit vapors to escape from the absorbent core (i.e., be breathable) while still preventing body fluids from passing through the backsheet.

The topsheet is compliant, soft feeling, and non-irritating to the wearer's skin. Further, the topsheet is fluid pervious permitting body fluids to readily penetrate through its thickness. A suitable topsheet can be manufactured in a wide variety of forms such as wovens and nonwovens; apertured formed films, hydroformed films; porous foams; reticulated films; and scrims. Preferred topsheets for use in absorbent articles of the present invention are selected from high loft nonwoven topsheets and apertured formed film topsheets. Apertured formed films are especially preferred for the topsheet because they are pervious to body fluids and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable methods for making formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel et al), issued Aug. 3, 1982; U.S. Pat. No. 4,463,045 (Ahr et al), issued Jul. 31, 1984; and U.S. Pat. No. 5,006,394 (Baird), issued Apr. 9, 1991. Each of these patents are incorporated herein by reference. Microapertured formed film topsheets and especially methods for making same are disclosed in U.S. Pat. No. 4,609,518 (Curro et al), issued Sep. 2, 1986 and U.S. Pat. No. 4,629,643 (Curro et al), issued Dec. 16, 1986, which are incorporated by reference.

The body surface of the formed film topsheet can be hydrophilic so as to help body fluids to transfer through the topsheet faster than if the body surface was not hydrophilic so as to diminish the likelihood that fluid will flow off the topsheet rather than flowing into and being absorbed by the absorbent structure. In a preferred embodiment, surfactant is incorporated into the polymer of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in U.S. Pat. No. 4,950,264 (Osborn) issued Aug. 21, 1990, which is incorporated herein by reference.

These trans-polymers or blends are also useful for carriers comprising a plurality of connected annular sections where each annular section is capable of releasably securing a container such as a bottle or can. These carriers are commonly referred to as "six-pack rings," although the carrier can typically comprise from two to twelve such annular rings, more typically from four to six rings. See, for example, U.S. Reissue Pat. No. 29,873 (Cunningham), reissued Jan. 2, 1979 and U.S. Pat. No. 3,938,656 (Owen), issued Feb. 17, 1976 (herein incorporated by reference), which disclose "six-pack rings" of various types.

These trans-polymers or blends can also be used as temporary coverings for the ground and are especially useful as agricultural mulch. These ground coverings are typically in the form of films or sheets that are spread out or otherwise applied to the ground to be covered. Ground coverings made from blends of these trans-polymers with starch can be particularly desirable since the covering should disintegrate relatively quickly with the residual trans-polymer ultimately biodegrading completely.

These trans-polymers or blends can also be used as biodegradable packaging materials for wrapping various products. These include edible products such as foods and beverages. Packaging materials made from blends of these trans-polymers with starch can be particularly desirable since these materials will disintegrate fairly rapidly if improperly discarded as litter and will ultimately biodegrade completely.

These trans-polymers or blends can also be used to deliver pesticides, insect repellents, herbicides, and the like. For example, when blended with suitable pesticides and shaped into a strip, these polymers can form biodegradable "flea collars." Similar blends formed into tags with a suitable attachment device can form biodegradable ear tags used for livestock to ward off flies and other insects. Suitable pesticides include the various chlorinated types such as Chlordane, pyrethroid/pyrethrin types such as Permethrin, organophosphates and carbamates such as Malathion and Carbaryl and Diazinon, repellents such as m-diethyl toluamide, diethylphenyl acetamide, and limonene, insect growth regulants such as Methoprene, Hydroprene, Fenvalerate, synergists such as piperonyl butoxide, and the like.

The polymers and blends of the present invention are also suitable for use as fibers or filaments in nonwovens. Fibers and filaments are interchangeable terms in the general sense, but where a more specific acknowledgment of length is appropriate, the term "fibers" is intended to refer to short filaments as in "staple fibers." These trans-polymers or blends can be converted to fibers or filaments by meltspinning techniques. Deniers of from about 2 to about 15 dpf are most common. The filaments can be used as-spun (undrawn) or in a stretched (drawn or oriented) condition. Drawing to reduce denier or for increasing orientation can be accomplished by the usual procedures.

Suitable thermoplastic fibers according to the present invention can be in the form of thermally bondable bicomponent fibers. As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers can provide thermal bonding by controlled melting of the sheath polymer, while retaining the desirable strength characteristics of the core polymer. An example of a biodegradable bicomponent fiber according to the present invention is a sheath made of trans-polyisoprene surrounding a core made from a higher melting biodegradable polymer such as polyvinyl alcohol or rayon.

These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e., unbent) or crimped (i.e., bent). Bicomponent fibers can be crimped by typical textile means such as, for example, a stuffer box method or the gear crimp method to achieve a predominantly two-dimensional or "flat" crimp.

Fibers made from polymers and blends of the present invention can be formed into nonwoven fabrics by a number of processes to provide spunbonded fabrics and fabrics made using staple fibers. Spunbonded nonwovens can be prepared by spinning and laying down simultaneously into webs of continuous filaments using known methods of distributing the threadline in the desired orientation in the web plane. Such webs can be thermally bonded under suitable conditions of time, temperature and pressure to yield strong fabrics with tensile properties that are usually superior to those obtained with staple webs. Bonding can also be carried out by using suitable adhesives and both these methods can be used to make point bonded or area bonded fabrics. Needle punching can also be used to give the webs stability and strength. Spunbonded fabrics can also be made by melt blowing these polymers or blends. In this process, a stream of the molten polymer or blend is extruded into a high velocity stream of heated dry air and a bonded web formed directly on a screen conveyor from the resultant fibers. Nonwoven fabrics can also be made by direct extrusion through a rotating die into a netlike product. See U.S. Pat. No. 5,219,646 (Gallagher et al), issued Jun. 15, 1993, which is incorporated.

These polymers or blends can also be used to make biodegradable foamed plastics. These include foamed containers, foamed packing components (e.g., "peanuts"), and the like. The foamed plastic can be made by compounding the polymer or blend with a suitable blowing agent such as pentane and then heating to volatilize the blowing agent. Typically, a surfactant suitable for stabilizing the air-liquid interface is employed as well. The foam can be used as is or can be cut into smaller pieces (commonly referred to as "peanuts") suitable as loose packaging filler.

Latexes made from these trans-polymers or blends are useful for biodegradable coatings and/or laminates such as those used to prepare glossy paper.

TENSILE AND TEAR PROPAGATION TEST METHODS

Tensile tests are performed according to ASTM D 882-83 with a 2 inch per minute rate of grip separation, or a modified test with a 20 inch per minute rate of grip separation. Tear propagation tests are performed according to ASTM D 1938-85 with a 10 inch per minute rate of grip separation. These tests are performed with the elongation occurring in the machine-direction of the film as formed (MD) as well as in the cross-direction (CD) of the film as formed. An Instron 1122 testing machine is used to conduct these tests, and the appropriate load cell (50 lb, 10000 g, 2000 g, or 500 g) is installed for the maximum force required. Instron Series IX software (version 4.1) is used to control the tensile or tear test and to analyze the resulting force-displacement data. A given sample thickness is determined by taking 5–7 measurements, evenly distributed over the 2" long×1" wide sample area, and averaging the measurements. The individual thickness measurements over the area of a given sample do not vary more than 10% from the average thickness.

SPECIFIC EXAMPLES

The following are specific examples of melt blown, extruded, compression molded, or solution cast films prepared according to the present invention:

Example 1

Preparation of Trans-1,4-Polyisoprene Melt Extruded Films

Trans-1,4-polyisoprene (TPI) in pellet form was obtained from Kuraray Inc., in Japan. The nominal molecular weight (M.W.) was listed as 400,000.

A melt extruded film is produced from the neat pellets using a Haake Rheomix Model 202 0.75 inch diameter single screw extruder equipped with a 6 inch wide horizontal sheet die having a 0.04 inch die gap. A constant taper screw having a 20:1 length to diameter ratio and a 3:1 compression ratio is employed. For the first extruded film trial (Sample 1), the temperature of the first heating zone is maintained at 140° C., the second heating zone at 160° C., and the die at 150° C. For the second extruded film trial (Sample 2), the temperature of the first heating zone is maintained at 160° C., the second heating zone at 180° C., and the die at 170° C. Screw speeds in both cases are maintained at 20 rpm. The molten film is passed from the die to a Postex sheet take-off system where it is cooled and collected on a cardboard core. The stack rolls are cooled with tap water at about 15° C. Take-off speed is adjusted to provide a film about 4.5 inches wide and 0.002 inches thick.

The tear propagation test is conducted on film Sample 2. The results are shown in Table 1 below:

TABLE 1

Tear Propagation Data for Film Sample 2

| Direction | Machine Mean | σ | Cross Mean | σ |
|---|---|---|---|---|
| Tear strength (g/mil) | 6.8 | 0.2 | 82.6 | 1.8 |

Tensile testing is also conducted on film Samples 1 and 2 with a crosshead speed of 20 inches per minute. The results are shown in Table 2 below.

TABLE 2

Tensile Data for Sample 1 and 2 Films

| Sample | 1 | | 1 | | 2 | | 2 | |
|---|---|---|---|---|---|---|---|---|
| Number of specimens | 5 | | 7 | | 4 | | 6 | |
| Av. Sample thickness (mm) | 0.070 | | 0.070 | | 0.070 | | 0.070 | |
| Direction | Machine | | Cross | | Machine | | Cross | |
| | Mean | σ | Mean | σ | Mean | σ | Mean | σ |
| Maximum Load (g) | 8435 | 2414 | 5306 | 531 | 8706 | 1340 | 4804 | 559 |
| Elongation at Max. Load (%) | 234 | 64 | 452 | 31 | 266 | 25 | 416 | 43 |
| Elongation at Break (%) | 273 | 107 | 454 | 31 | 268 | 25 | 418 | 43 |
| Load at 5% Elongation (g) | 1752 | 449 | 1221 | 69 | 1941 | 160 | 1209 | 153 |
| Load at 10% Elongation (g) | 2215 | 220 | 1112 | 73 | 2277 | 72 | 1137 | 145 |
| Load at 25% Elongation (g) | 2430 | 187 | 950 | 69 | 2477 | 83 | 958 | 122 |
| Load at Break (g) | 4994 | 2060 | 4039 | 1485 | 6308 | 2164 | 2290 | 1780 |

Example 2

Preparation of Trans-1,4-Polyisoprene Melt Blown Films

The neat trans-1,4-polyisoprene (TPI) pellets are repelletized using the single-screw extruder described above equipped with a single-strand horizontal rod die and a 0.125 inch diameter nozzle. The temperature of the first heating zone is maintained at 150° C., the second heating zone at 170° C., and the die at 150° C. The screw speed is held constant at 45 rpm. The molten strand is cooled and solidified in a water bath held at about 15° C. prior to entering a Berlyn Model PEL-2 pelletizer where it is chopped into pellets approximately 0.125 inches long.

Melt blown film is produced from the repelletized material using a Haake Rheomix TW-100 twin-screw extruder with conical barrels and two partially intermeshing counterrotating venting screws and equipped with a 1 inch spiral die and a 12 inch air cooling ring. The temperature of the first heating zone is maintained at 160° C., the second heating zone at 180° C., and the third heating zone at 190° C. The first die zone is maintained at 180° C., and the second die zone at 170° C. The screw speed is held constant at 25 rpm. The molten tube is passed from the die and is inflated by blowing air into the tube through an air duct inside the die. The inflated tube is cooled by chilled air from the air cooling ring, and then collapsed by a set of nip rolls at the top of the blown film take-off tower. The collapsed tube is then collected on a cardboard core. The blow-up ratio (ratio of the bubble diameter to the die exit diameter) and the vertical take-off speed are adjusted to provide a film tube about 3 inches in diameter and 0.002 inches thick.

Tear propagation tests are conducted on the melt blown film. The results are shown in Table 3 below:

TABLE 3

Tear Propagation Data for Melt Blown Film

| Direction | Machine Mean | σ | Cross Mean | σ |
|---|---|---|---|---|
| Tear strength (g/mil) | 10.2 | 0.6 | 27.6 | 1.4 |

Tensile testing is conducted with a crosshead speed of 20 inches per minute. The results are shown in Table 4 below:

TABLE 4

Tensile Data for Melt Blown Film

| Number of specimens | 4 | | 7 | |
|---|---|---|---|---|
| Direction | Machine | | Cross | |
| | Mean | σ | Mean | σ |
| Maximum Load | 3633 | 332 | 4217 | 598 |
| Elongation at Maximum Load (%) | 315 | 50 | 341 | 25 |
| Elongation at Break (%) | 317 | 50 | 342 | 25 |
| Load at 5% Elongation (g) | 742 | 193 | 794 | 76 |
| Load at 10% Elongation (g) | 1069 | 193 | 790 | 47 |
| Load at 25% Elongation (g) | 1144 | 179 | 802 | 71 |
| Load at Break | 2628 | 1384 | 2614 | 842 |

Example 3
Preparation of Trans-1,4-Polyisoprene Solution Cast Films

Approximately 5 g of the neat pellets are cut into small pieces by means of a small Thomas-Wiley® laboratory mill, and are dissolved by adding them slowly to about 250 mL of stirred tetrahydrofuran (THF) heated to approximately 60° C. on a laboratory hotplate equipped with a magnetic stirrer. Upon dissolution of the polymer, the solution is allowed to cool to room temperature. An appropriate amount of this solution (approximately 50–80 mL) is poured onto a clean flat glass plate measuring 20 cm×20 cm such that the solution covers the entire surface of the plate. The THF is allowed to evaporate slowly by covering the plate with a suitable cover, the rate of evaporation being controlled by a relatively small hole in the cover. After the solvent has completely evaporated (24 hours), the resultant cast polymer film is peeled of the glass plate and cut into strips 1 inch wide. The thickness of the film is controlled by varying the concentration of the solution and the volume of solution applied to the glass plate.

Tensile testing is conducted with a crosshead speed of 20 inches per minute. The results are reported in Table 5 below:

The results are shown in Table 6 below:

TABLE 6

Film Quality Data for TPI Blends

| Sample | Wt % TPI | Other Polymer* | Wt % Other Polymer | Film Quality | Blend Temp. (°C.) |
|---|---|---|---|---|---|
| 1 | 70 | Cis-1,4-polyisoprene | 30 | good | 150 |
| 2 | 80 | Cis-1,4-polyisoprene | 20 | good | 150 |
| 3 | 70 | Cornstarch | 30 | good | 150 |
| 4 | 70 | Mater-Bi AF05H | 30 | good | 150 |
| 5 | 70 | Polycaprolactone | 30 | good | 150 |
| 6 | 70 | Polyurethane #1 | 30 | good | 170 |
| 7 | 70 | Polyurethane #2 | 30 | good | 170 |
| 8 | 70 | Polyester | 30 | good | 160 |
| 9 | 80 | PHBV | 20 | moderate | 160 |
| 10 | 70 | PHBV | 30 | poor | 160 |
| 11 | 70 | Poly(vinyl alcohol) | 30 | poor | 200 |
| 12 | 70 | Cellulose | 30 | poor | 190 |
| 13 | 70 | Cellulose acetate propionate | 30 | poor | 190 |

TABLE 5

Tensile Data for Solution Cast Films.

| Sample | BC-1 | | BC-2 | | BC-4 | | BC-5 | | BC-6 | |
|---|---|---|---|---|---|---|---|---|---|---|
| Number of specimens | 2 | | 4 | | 4 | | 5 | | 5 | |
| Av. Sample thickness (mm) | 0.030 | | 0.070 | | 0.040 | | 0.040 | | 0.035 | |
| | Mean | σ | Mean | σ | Mean | σ | Mean | σ | Mean | σ |
| Maximum Load (g) | 1223 | 6 | 3675 | 205 | 1539 | 146 | 1626 | 71 | 1346 | 117 |
| Elongation at Max. Load (%) | 260 | 25 | 310 | 17 | 195 | 38 | 223 | 12 | 644 | 38 |
| Elongation at Break (%) | 262 | 25 | 312 | 17 | 197 | 39 | 224 | 12 | 645 | 38 |
| Load at 5% Elongation (g) | 424 | 62 | 994 | 96 | 663 | 47 | 588 | 43 | 495 | 13 |
| Load at 10% Elongation (g) | 494 | 114 | 1322 | 65 | 829 | 47 | 757 | 41 | 623 | 14 |
| Load at 25% Elongation (g) | 521 | 95 | 1457 | 24 | 915 | 64 | 839 | 45 | 633 | 13 |
| Load at Break (g) | 1041 | 130 | 2281 | 1174 | 1407 | 89 | 1141 | 415 | 886 | 311 |

Example 4
Preparation of Blends of Trans-1,4-Polyisoprene and Other Polymers

A) Compression Molded Film Blends

Approximately 50 grams of a mixture comprising 70 or 80% by weight trans-1,4-polyisoprene, the balance being another polymer, are added to and melt blended in a Haake Rheomix 600 batch mixer equipped with roller style rotors. The chamber is heated to a temperature sufficient to mix both polymers (see Table I below). The mixture of polymers are blended at 60 rpm for 10 minutes. The chamber is then opened and the blended polymers removed with the aid of a spatula.

Approximately one gram of each polymer blend is placed between two thin sheets of polytetrafluoroethylene (Teflon®), the whole being placed between the platens of a Carver® hydraulic laboratory press. The platens are heated to the blending temperature and sufficient pressure is applied so as to cause the polymer blend to flow into a thin film with a thickness of approximately 0.005 inches. The pressure is released and the polymer film allowed to cool to room temperature before removing the outer polytetrafluoroethylene sheets. The mechanical integrity of each of the films is readily discerned by simply stretching the film sample by hand.

As shown in Table 3 above, acceptable films can be made from blends of TPI with various other biodegradable polymers. While acceptable films from blends of TPI and poly(vinyl alcohol), cellulose, and cellulose acetate propionate (see Samples 11–13) could not be made at the ratios tested, it is expected that acceptable films could be made from these blends, especially at higher levels of TPI.

B) Melt Extruded Film Blends

1) Trans-1,4-Polyisoprene Blended with Cis-1,4-Polyisoprene

A melt extruded film containing 75% by weight trans-1,4-polyisoprene and 25 by weight cis-1,4-polyisoprene (TPI/CPI) is prepared by first melt compounding a total of about 800 grams of the two polymers using the single-screw extruder described in Example 1 equipped with a single-strand horizontal rod die and a 0.125 inch diameter nozzle. The temperature profile of the extruder is varied from 150° C. in the first heating zone, to 160° C. in the second heating zone at the discharge end near the die, to 150° C. in the third heating zone. The screw speed is maintained at 30 rpm. The molten strand is cooled and solidified in a water bath at about 15° C. prior to entering a Berlyn Model PEL-2 pelletizer where it is chopped into pellets approximately 0.125 inches long.

Extruded film is produced from the compounded pellets using the twin-screw extruder described in Example 2 equipped with a 6 inch wide horizontal sheet die having a 0.04 inch die gap. The temperature of the first heating zone is maintained at 130° C., the second heating zone at 150° C., and the third heating zone at 160° C. The die is maintained at 150° C., and the screw speed is held constant at 15 rpm. The molten film is passed from the die to a Postex sheet take-off system where it is cooled and collected on a cardboard core. The stack rolls are cooled with tap water at about 15° C. The take-off speed is adjusted to provide a film about 4.5 inches wide and 0.002 inches thick.

2) Trans-1,4-Polyisoprene Blended with Mater-Bi AF05H

A melt extruded cast film blend containing 70% by weight of the repelletized trans-1,4-polyisoprene (see Example 1 above) and 30% by weight Mater-Bi AF05H (a starch based interpenetrating network) (TPI/Starch) is prepared by first melt compounding a total of about 800 grams of the polymers using the twin screw extruder described in Example 2 equipped with a single-strand horizontal rod die and a 0.125 inch diameter nozzle. The temperature of the first heating zone is maintained at 120° C., the second heating zone at 140° C., and the third heating zone at 150° C. The die is maintained at 140° C., and the screw speed is held constant at 35 rpm. The molten strand is cooled and solidified in a water bath at about 15° C. prior to entering a Berlyn Model PEL-2 pelletizer where it is chopped into pellets approximately 0.125 inches long.

The extruded film is produced from the compounded pellets using the Haake Rheomix TW-100 twin-screw extruder equipped with a 6 inch wide horizontal sheet die having a 0.04 inch die gap. The temperature of the first heating zone is maintained at 120° C., the second heating zone at 140° C., and the third heating zone at 150° C. The die is maintained at 140° C., and the screw speed was held constant at 20 rpm. The molten film is passed from the die to a Postex sheet take-off system where it is cooled and collected on a cardboard core. The stack rolls are cooled with tap water at about 15° C. The take-off speed is adjusted to provide a film about 4.5 inches wide and 0.002 inches thick.

Tensile tests are performed on these polymer blends with a crosshead speed of 2 inches per minute and tear test with a crosshead speed of 10 inches per minute. The results are shown in Table 7 below:

TABLE 7

Tensile Data for Melt Extruded TPI Blend Films

| PROPERTY: | TPI/CPI | | | | TPI/Starch | | | |
|---|---|---|---|---|---|---|---|---|
| | MD | | CD | | MD | | CD | |
| Average thickness (mil) | 2.0 | | 2.0 | | 2.0 | | 2.0 | |
| | Mean | σ | Mean | σ | Mean | σ | Mean | σ |
| Tensile modulus (MPa) | 161 | 5 | 243 | 27 | 278 | 48 | 251 | 22 |
| Ultimate elongation (%) | 287 | 19 | 480 | 27 | 121 | 36 | 107 | 20 |
| Tensile strength (MPa) | 34.7 | 3.3 | 14.1 | 1.6 | 18.4 | 4.9 | 4.4 | 0.4 |
| Tear strength (g/mil) | 5.2 | 0.4 | 69.9 | 1.5 | 3.8 | 0.2 | 74.5 | 3.4 |

Example 5
Biodegradability of Polymers

Representative polymers are submitted for Sturm testing (Weston Labs of Pennsylvania). These test results are shown in Table 8 below:

TABLE 8

Biodegradation Data

| Sample | Test Material | M.W. | Elapsed Time (days) | % Mineralization |
|---|---|---|---|---|
| 1 | Glucose | 180 | 91 | 98.3 |
| 2 | polyvinyl alcohol | 50,000 | 91 | 22.2 |
| 3 | cis-1,4-polyisoprene | 800,000 | 91 | 9.6 |
| 4 | cis-1,4-polyisoprene | 10,000 | 91 | 37.3 |
| 5 | trans-1,4-polyisoprene | 400,000 | 91 | 28.2 |

Glucose (Sample 1) is a positive control representing a very rapidly biodegradable low molecular weight substance. Polyvinyl alcohol (Sample 2) is a reference polymer that is generally regarded as biodegradable. Cis-1,4-polyisoprene (Samples 3 and 4) is for comparison.

It is important to note that the surface areas of the samples placed in this test were not determined. Because the rate of biodegradation in this test is impacted in part by the surface area of the sample, the different levels of mineralization for the various polymers do not necessarily correlate to their relative biodegradability. Even so, any of materials that exceeds 5% mineralization in 90 days is considered to be inherently biodegradable.

What is claimed is:

1. A biodegradable article which is selected from the group consisting of fluid pervious disposable absorbent article topsheets, disposable absorbent article backsheets, nonwovens, thermally bondable bicomponent fibers, adhesive tape substrates, laminates, surgical sponges, tampon applicators, disposable syringes, toys, bags, containers, carriers comprising a plurality of connected annular sections wherein each annular section is capable of releasably securing a container, disposable garments, disposable surgical drapes, agricultural mulch, agricultural products containing seeds, pesticides or herbicides, and foamed plastic products, said article at least partially comprising a thermoplastic trans-polymer having a weight average molecular weight ($M_w$) of at least about 20,000 and made by polymerizing a monomer component that comprises:

(1) from about 70 to 100 mole % 1,3-dienes selected from the group consisting of 1,3-butadiene, isoprene, 2,3-dimethyl-1,3-butadiene, 2-methyl-3-ethyl-1,3-butadiene, 2-methyl-3-propyl-1,3-butadiene, 2-phenyl-1,3-butadiene, 2,3-diphenyl-1,3-butadiene, 1,3-pentadiene, 2-methyl-1,3-pentadiene, 2,3-dimethyl-1,3-pentadiene, 2-methyl-3-ethyl-1,3-pentadiene, 2-methyl-3-propyl-1,3-pentadiene, 1,3-hexadiene, beta-myrcene, ocimene, and mixtures thereof; and (2) from 0 mol % to about 30 mole % compatible comonomers.

2. The article of claim 1 wherein said monomer component comprises from about 80 to 100 mole % of said 1,3-diene and from 0 to about 20 mole % of said comonomer.

3. The article of claim 2 wherein said monomer component comprises from about 90 to 100 mole % of said 1,3-diene and from 0 to about 10 mole % of said comonomer.

4. The article of claim 2 wherein said 1,3-diene is selected from the group consisting of isoprene, 1,3-butadiene and 2,3-dimethyl-1,3-butadiene.

5. The article of claim 4 wherein said 1,3-diene is isoprene.

6. The article of claim 2 wherein said trans-polymer has a $M_w$ in the range of from about 50,000 to about 1,000,000.

7. The article of claim 6 wherein said trans-polymer has a $M_w$ in the range of from about 200,000 to about 600,000.

8. The article of claim 1 which is selected from the group consisting of fluid pervious disposable absorbent article topsheets, disposable absorbent article backsheets, nonwovens, thermally bondable bicomponent fibers, laminates, tampon applicators, and agricultural mulch.

9. A biodegradable polymer-containing composition which comprises:
   a. from about 20 to about 99% by weight of a thermoplastic trans-polymer having a weight average molecular weight ($M_w$) of at least about 20,000 and made by polymerizing a monomer component that comprises:
      (1) from about 70 to 100 mole % 1,3-dienes selected from the group consisting of 1,3-butadiene, isoprene, 2,3-dimethyl-1,3-butadiene, 2-methyl-3-ethyl-1,3-butadiene, 2-methyl-3-propyl-1,3-butadiene, 2-phenyl-1,3-butadiene, 2,3-diphenyl-1,3-butadiene, 1,3-pentadiene, 2-methyl-1,3-pentadiene, 2,3-dimethyl-1,3-pentadiene, 2-methyl-3-ethyl-1,3-pentadiene, 2-methyl-3-propyl-1,3-pentadiene, 1,3-hexadiene, beta-myrcene, ocimene, and mixtures thereof; and
      (2) from 0 to about 30 mole % compatible comonomers; and
   b. from about 1 to about 80% by weight of another biodegradable component.

10. The composition of claim 9 wherein said monomer component comprises from about 80 to 100 mole % of said 1,3-diene and from 0 to about 20 mole % of said comonomer.

11. The composition of claim 10 wherein said monomer component comprises from about 90 to 100 mole % of said 1,3-diene and from 0 to about 10 mole % of said comonomer.

12. The composition of claim 10 wherein said 1,3-diene is selected from the group consisting of isoprene, 1,3-butadiene and 2,3-dimethyl-1,3-butadiene.

13. The composition of claim 12 wherein said 1,3-diene is isoprene.

14. The composition of claim 10 wherein said trans polymer has a $M_w$ in the range of from about 50,000 to about 1,000,000.

15. The article of claim 14 wherein said trans polymer has a $M_w$ in the range of from about 200,000 to about 600,000.

16. The composition of claim 10 wherein said biodegradable component comprises a biodegradable polymer selected from the group consisting of polyvinyl alcohol, hydrolyzable aliphatic polyesters, hydrolyzable aliphatic polyurethanes, cis-polyisoprene, cis-polybutadiene, poly (caprolactone), poly(lactic acid), poly(hydroxy alkanoates), natural rubber, gutta percha, balata, dextran, chitin, chitosan, cellulose, cellulose esters, starch, and mixtures thereof.

17. The composition of claim 16 wherein said biodegradable polymer is starch.

18. The composition of claim 16 wherein said biodegradable polymer is cis-polyisoprene.

19. The composition of claim 10 which comprises from about 30 to about 95% by weight of said trans-polymer and from about 5 to about 70% by weight of said biodegradable component.

20. The composition of claim 19 which comprises from about 50 to about 90% by weight of said trans-polymer and from about 10 to about 50% by weight of said biodegradable component.

21. A biodegradable article made from the composition of claim 9 and which is selected from the group consisting of fluid pervious disposable absorbent article topsheets, disposable absorbent article backsheets, nonwovens, thermally bondable bicomponent fibers, adhesive tape substrates, laminates, surgical sponges, tampon applicators, disposable syringes, toys, bags, containers, carriers comprising a plurality of connected annular sections wherein each annular section is capable of releasably securing a container, disposable garments, disposable surgical drapes, agricultural mulch, agricultural products containing seeds, pesticides or herbicides, and foamed plastic products.

22. An absorbent article, which comprises
   I. a fluid pervious topsheet;
   II. a backsheet,
   III. an absorbent core positioned between said topsheet and backsheet
   IV. wherein at least one of said topsheet and backsheet are a film or nonwoven made from:
      A. a thermoplastic trans-polymer having a weight average molecular weight ($M_w$) in the range of from about 50,000 to about 1,000,000 and made by polymerizing a monomer component that comprises:
         (1) from about 80 to 100 mole % 1,3-dienes selected from the group consisting of 1,3-butadiene, isoprene and 2,3-dimethyl-1,3-butadiene; and
         (2) from 0 to about 20 mole % compatible comonomers; or
      B. a combination of:
         (1) from about 30 to about 95% by weight of said trans-polymer; and
         (2) from about 5 to about 70% by weight of another biodegradable component comprising a biodegradable polymer selected from the group consisting of polyvinyl alcohol, hydrolyzable aliphatic polyesters, hydrolyzable polyurethanes, cis-polyisoprene, cis-polybutadiene, poly (caprolactone), poly(lactic acid), poly (hydroxy alkanoates), natural rubber, gutta percha, balata, dextran, chitin, chitosan, cellulose, cellulose esters, starch, and mixtures thereof.

23. The article of claim 22 wherein said monomer component comprises from about 90 to 100 mole % of said 1,3-diene and from 0 to about 10 mole % of said comonomer.

24. The article of claim 23 wherein said 1,3-diene is isoprene.

25. The article of claim 24 wherein said biodegradable component is cis-polyisoprene.

26. The article of claim 24 wherein said biodegradable polymer is starch.

27. The article of claim 22 which comprises from about 50 to about 90% by weight of said trans-polymer and from about 10 to about 50% by weight of said biodegradable component.

28. A method for applying a temporary covering to the ground which comprises the step of applying to the ground a biodegradable covering which is made from:
   A. a thermoplastic trans-polymer having a weight average molecular weight ($M_w$) in the range of from about 50,000 to about 1,000,000 and made by polymerizing a monomer component that comprises:
      (1) from about 80 to 100 mole % 1,3-dienes selected from the group consisting of 1,3-butadiene, isoprene, 2,3-dimethyl-1,3-butadiene, 2-methyl-3-ethyl-1,3-butadiene, 2-methyl-3-propyl-1,3-butadiene, 2-phenyl-1,3-butadiene, 2,3-diphenyl-1,3-butadiene, 1,3-pentadiene, 2-methyl-1,3-pentadiene, 2,3- dimethyl-1,3-pentadiene, 2-methyl-3-ethyl-1,3-pentadiene, 2-methyl-3-propyl-1,3-pentadiene, 1,3-hexadiene, beta-myrcene, ocimene, and mixtures thereof; and
   (2) from 0 to about 20 mole % compatible comonomers; or
B. a combination of:
   (1) from about 20 to about 99% by weight of said trans-polymer; and
   (2) from about 1 to about 80% by weight of another biodegradable component.

29. The method of claim 28 wherein the monomer component comprises from about 90 to 100 mole % of the 1,3-diene and from 0 to about 10 mole % of the comonomer.

30. The method of claim 28 wherein the 1,3-diene is selected from the group consisting of isoprene, 1,3-butadiene and 2,3-dimethyl-1,3-butadiene.

31. The method of claim 30 wherein the 1,3-diene is isoprene.

32. The method of claim 30 wherein the biodegradable component comprises a biodegradable polymer selected from the group consisting of polyvinyl alcohol, hydrolyzable aliphatic polyesters, hydrolyzable polyurethanes, cis-polyisoprene, cis-polybutadiene, poly(caprolactone), poly(lactic acid), poly(hydroxy alkanoates), natural rubber, gutta percha, balata, dextran, chitin, chitosan, cellulose, cellulose esters, starch, and mixtures thereof.

33. The method of claim 32 wherein the biodegradable polymer is cis-polyisoprene.

34. The method of claim 32 wherein the biodegradable polymer is starch.

35. The method of claim 29 which comprises from about 30 to about 95% by weight of the trans-polymer and from about 5 to about 70% by weight of the biodegradable component.

36. A packaged product which is wrapped in a packaging material which is made from:
A. a thermoplastic trans-polymer having a weight average molecular weight ($M_w$) in the range of from about 50,000 to about 1,000,000 and made by polymerizing a monomer component that comprises:
   (1) from about 80 to 100 mole % 1,3-dienes selected from the group consisting of 1,3-butadiene, isoprene, 2,3-dimethyl-1,3-butadiene, 2-methyl-3-ethyl-1,3-butadiene, 2-methyl-3-propyl-1,3-butadiene, 2-phenyl-1,3-butadiene, 2,3-diphenyl-1,3-butadiene, 1,3-pentadiene, 2-methyl-1,3-pentadiene, 2,3-dimethyl-1,3-pentadiene, 2-methyl-3-ethyl-1,3-pentadiene, 2-methyl-3-propyl-1,3-pentadiene, 1,3-hexadiene, beta-myrcene, ocimene, and mixtures thereof; and
   (2) from 0 mol % to about 20 mole % of compatible comonomers; or
B. a combination of:
   (1) from about 30 to about 95% by weight of said trans-polymer; and
   (2) from about 5 to about 70% by weight of another biodegradable component.

37. The product of claim 36 wherein said monomer component comprises from about 90 to 100 mole % of said 1,3-diene and from 0 to about 10 mole % of said comonomer.

38. The product of claim 37 wherein said 1,3-diene is selected from the group consisting of isoprene, 1,3-butadiene and 2,3-dimethyl-1,3-butadiene.

39. The product of claim 38 wherein said 1,3-diene is isoprene.

40. The product of claim 37 wherein said biodegradable component comprises a biodegradable polymer selected from the group consisting of polyvinyl alcohol, hydrolyzable aliphatic polyesters, hydrolyzable polyurethanes, cis-polyisoprene, cis-polybutadiene, poly(caprolactone), poly(lactic acid), poly(hydroxy alkanoates), natural rubber, gutta percha, balata, dextran, chitin, chitosan, cellulose, cellulose esters, starch, and mixtures thereof.

41. The product of claim 40 wherein said biodegradable polymer is cis-polyisoprene.

42. The product of claim 40 wherein said biodegradable polymer is starch.

43. The product of claim 37 which comprises from about 30 to about 95% by weight of said trans-polymer and from about 5 to about 70% by weight of said biodegradable component.

44. The product of claim 43 which comprises from about 50 to about 90% by weight of said trans-polymer and from about 10 to about 50% by weight of said biodegradable component.

45. A method for packaging a product which comprises wrapping the product in a packaging material which is made from:
A. a thermoplastic trans-polymer having a weight average molecular weight ($M_w$) in the range of from about 50,000 to about 1,000,000 and made by polymerizing a monomer component that comprises:
   (1) from about 90 to 100 mole % 1,3-dienes selected from the group consisting of 1,3-butadiene, isoprene and 2,3-dimethyl-1,3-butadiene; and
   (2) from 0 to about 10 mole % compatible comonomers; or
B. a combination of:
   (1) from about 50 to about 90% by weight of said trans-polymer; and
   (2) from about 10 to about 50% by weight of another biodegradable component comprising a biodegradable polymer selected from the group consisting of polyvinyl alcohol, hydrolyzable aliphatic polyesters, hydrolyzable polyurethanes, cis-polyisoprene, cis-polybutadiene, poly(caprolactone), poly(lactic acid), poly(hydroxy alkanoates), natural rubber, gutta percha, balata, dextran, chitin, chitosan, cellulose, cellulose esters, starch, and mixtures thereof.

46. The method of claim 45 wherein the 1,3-diene is isoprene.

47. The method of claim 46 wherein the biodegradable polymer is cis-polyisoprene.

48. The method of claim 46 wherein the biodegradable polymer is starch.

49. A method for making a biodegradable foamed plastic which comprises foaming:
A. a thermoplastic trans-polymer having a weight average molecular weight ($M_w$) in the range of from about 50,000 to about 1,000,000 and made by polymerizing a monomer component that comprises:
   (1) from about 80 to 100 mole % 1,3-dienes selected from the group consisting of 1,3-butadiene, isoprene and 2,3-dimethyl-1,3-butadiene; and
   (2) from 0 to about 20 mole % compatible comonomers; or
B. a combination of:
   (1) from about 30 to about 95% by weight of said trans-polymer; and
   (2) from about 5 to about 75% by weight of another biodegradable component comprising a biodegradable polymer selected from the group consisting of polyvinyl alcohol, hydrolyzable aliphatic polyesters, hydrolyzable polyurethanes, cis-polyisoprene, cis-polybutadiene, poly(caprolactone), poly(lactic acid), poly(hydroxy alkanoates), natural rubber, gutta percha, balata, dextran, chitin, chitosan, cellulose, cellulose esters, starch, and mixtures thereof.

50. The method of claim 49 wherein the monomer component comprises from about 90 to 100 mole % of the 1,3-diene and from 0 to about 10 mole % of the comonomer.

51. The method of claim 50 wherein the 1,3-diene is isoprene.

52. The method of claim 50 wherein the biodegradable polymer is cis-polyisoprene.

53. The method of claim 50 wherein the biodegradable polymer is starch.

54. The method of claim 49 which comprises from about 50 to about 90% by weight of the trans-polymer and from about 10 to about 50% by weight of the biodegradable component.

* * * * *